(12) United States Patent
Dunn et al.

(10) Patent No.: US 7,597,676 B2
(45) Date of Patent: Oct. 6, 2009

(54) MALLEOLAR PAD

(75) Inventors: Raymond M. Dunn, Shrewsbury, MA (US); Richard M. Beane, Hingham, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 11/040,492

(22) Filed: Jan. 21, 2005

(65) Prior Publication Data

US 2005/0165340 A1 Jul. 28, 2005

Related U.S. Application Data

(60) Provisional application No. 60/538,400, filed on Jan. 22, 2004.

(51) Int. Cl.
*A61F 13/00* (2006.01)
(52) U.S. Cl. .............. 602/65; 602/53; 602/60; 602/61; 602/62
(58) Field of Classification Search ............ 602/65, 602/79, 53, 60–62, 20, 23, 17; 128/888, 128/889, 96.1
See application file for complete search history.

(56) References Cited

U.S. PATENT DOCUMENTS

| | | | | |
|---|---|---|---|---|
| 3,266,058 A | * | 8/1966 | Guttman | 2/239 |
| 4,590,932 A | * | 5/1986 | Wilkerson | 602/65 |
| 5,115,801 A | * | 5/1992 | Cartmell et al. | 602/48 |
| 5,185,000 A | * | 2/1993 | Brandt et al. | 602/63 |
| 5,879,292 A | * | 3/1999 | Sternberg et al. | 600/300 |
| 6,287,253 B1 | * | 9/2001 | Ortega et al. | 600/300 |
| 6,306,107 B1 | * | 10/2001 | Myklebust et al. | 600/587 |
| 6,646,556 B1 | | 11/2003 | Smith et al. | |
| 7,027,358 B1 | | 4/2006 | Esposito et al. | |
| 7,030,764 B2 | | 4/2006 | Smith et al. | |
| 2002/0095105 A1 | * | 7/2002 | Jensen | 602/27 |
| 2004/0158283 A1 | * | 8/2004 | Shook et al. | 606/201 |
| 2005/0004500 A1 | * | 1/2005 | Rosser et al. | 602/41 |
| 2005/0165284 A1 | * | 7/2005 | Gefen | 600/300 |

\* cited by examiner

*Primary Examiner*—Kim M Lewis
(74) *Attorney, Agent, or Firm*—Weingarten, Schurgin, Gagnebin & Lebovici LLP

(57) ABSTRACT

The malleolar pad of preferred embodiments of the present invention provides a treating physician with the ability to monitor pressure at a wound site, adjust the pressure to more accurately treat and facilitate healing of, for example, a pressure ulcer while providing adequate wound care. Pressure ulcers can have varied presentations with respect to open sores and the location of the wound. Thus, proper fixation methods provided by monitoring the pressure measurement devices which allow adjustment of the compressive forces applied by the malleolar pad provide rewarding outcomes for the patient and the physician.

18 Claims, 6 Drawing Sheets

MALLEOLAR PAD

CROSS REFERENCE TO RELATED APPLICATIONS

The present application claims the benefit of U.S. Provisional Application No. 60/538,400, filed Jan. 22, 2004. The entire contents of the above application is incorporated herein by reference.

BACKGROUND OF THE INVENTION

Venous disease is a main cause of pressure ulcers such as, for example, leg ulcers. Venous disease occurs when the valves in the circulatory system that control the flow of blood up the leg, as it travels from the foot to the heart, become damaged. If the valves are damaged the blood can backflow causing high pressure in the veins. Under these conditions fluids that are normally retained in the veins leak out, resulting in swelling in the legs. This swelling prevents oxygen, which is carried in the blood and necessary for the healing process, from reaching the wound site.

By way of further details and definitions, the two major superficial veins of the lower extremities are the great saphenous and small saphenous veins. The great saphenous vein, a superficial vein, runs generally medially and distally from the knee to the foot. The small saphenous vein continues into the foot and runs posteriorly and inferiorly with respect to the lateral malleolus. The great saphenous vein runs anteriorly and in proximity to the medial malleolus joining the posterior arch vein which runs posteriorly and inferiorly to the medial malleolus. The great saphenous vein communicates with the dorsal venous arch, a superficial vein of the foot.

The superficial veins are generally near the surface and communicate with deep veins which are further from the surface. Perforating veins are the veins which connect the superficial veins to the deep veins. The deep veins of the foot include the deep plantar venous arch, the medial and lateral plantar veins, and the posterior tibial veins. The deep veins of the leg include the posterior tibial veins, the peroneal veins and the anterior tibial veins. The fascia is a sheet or band of tissue which connects the muscle and deep veins and holds them together. The perforating veins are communications between the superficial veins (above the deep fascia and near the skin) and the deep veins below the fascia. The deep and superficial veins possess valves which permit unidirectional flow in the direction of the heart. The perforating veins also possess valves which permit unidirectional blood flow from the superficial veins to the deep veins. The perforating veins pass through the fascia. Venous return to the heart is assisted by the pumping action of the muscles which compress the deep veins and force blood toward the heart during contraction. If the valves in the perforating veins become incompetent or if the deep veins become blocked, pressure in the superficial veins increases resulting in hyperpigmentation, eczema, edema, varicosities and/or skin ulcerations. As a result venous ulcers occur in the lower limbs of patients resulting from venous insufficiency due to deep vein thrombosis and failure of the venous valves that normally act during muscle contraction to prevent blood backflow.

The result of chronic venous insufficiency at the ankle level has traditionally been that of chronic swelling, thickening of the skin, discoloration of the skin, and ultimately ulceration. Venous stasis ulcers appear as skin ulcerations on the lower extremities of a person, i.e. the leg, ankle or foot and in particular in a location posterior to the malleolus. One cause of venous stasis is valvular insufficiency in the deep veins, perforating veins and superficial veins. Stasis means a stoppage of flow of blood. Impaired blood flow interferes with normal healing and prolongs repair. Patient care therefore centers on preventing infection, increasing blood flow to deep veins, and decreasing pressure to superficial veins.

Compression therapy is often used to treat and/or prevent venous ulcers with the rationale that if the excess fluid can be squeezed out, oxygen can return and facilitate the healing of the wound. Compression therapy involves wrapping the leg with elastic bandages that apply a constant uniform pressure. For the best treatment the wrapping is applied so there is approximately 20-40 mmHg of pressure. However, as every leg is different this can be difficult to achieve.

There still exists a need for a device for treating pressure ulcers, for example, venous ulcers and similar pathology which accurately and reliably provides the appropriate wound care, compression force and provides a measure of the pressure being applied.

SUMMARY OF THE INVENTION

The malleolar pad of preferred embodiments of the present invention provides a treating physician with the ability to monitor pressure at a wound site, adjust the pressure to more accurately treat and facilitate healing of, for example, a pressure ulcer while providing adequate wound care. Pressure ulcers can have varied presentations with respect to open sores and the location of the wound. Thus, proper fixation methods provided by monitoring the pressure measurement devices which allow adjustment of the compressive forces applied by the malleolar pad provide rewarding outcomes for the patient and the physician.

In a preferred embodiment of the present invention, the malleolar pad is a composite device incorporating structure for wound care, is sterilizable, reusable and is able to wick moisture or fluids away from the wound site to a remote outer layer or to a conduit.

In accordance with a preferred embodiment, a malleolar pad for treating a wound site in a region of the body includes a compression wrapping for securing the malleolar pad with the region of the body, a plurality of layers to facilitate treatment of the wound site, and at least one pressure measurement device positioned in the malleolar pad to provide a measure of pressure applied to a location proximate the wound site. The plurality of layers include an adherent layer, a non-adherent layer proximate the adherent layer, a wicking layer, at least two shell layers and a filler layer disposed between the at least two shell layers. The filler layer includes a gel, for example, silicon gel or other filler materials. The wicking layer is in fluid communication with a conduit to remove fluid from the wound site.

The malleolar pad includes a pressure measurement device having at least one of an analog readout or a digital readout. The pad can be placed proximate to the malleolar, to the elbow, to the back of the head (occipital), to the upper back (scapular) and to the lower back (sacrum). The layers of the pad are formed of bio-compatible material.

In accordance with another aspect of the present invention, a preferred embodiment includes a method of treating a pressure ulcer comprising the steps of placing a malleolar pad having a plurality of layers and a pressure measurement device proximate to a region of the body having the pressure ulcer; applying an initial pressure to the pressure ulcer, measuring the pressure at the pressure ulcer, and augmenting the pressure to the pressure ulcer if the initial pressure is below a prescribed treatment level.

The foregoing and other objects, features and advantages of the malleolar pad will be apparent from the following more particular description of preferred embodiments of the malleolar pad, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

The preferred embodiments of the present invention are directed at a malleolar pad that provides for wound care, and applies appropriate compressive force around a pressure ulcer, for example, around an ankle while augmenting the compressive force to a wound site. A pressure measurement device is provided in the pad to provide a measure of the pressure applied for compression therapy. In a preferred embodiment, the pressure measurement device is integral with the pad and monitors continuous pressure applied at a particular wound site. By monitoring the pressure measurement, adjustments to the compressive force can be made so that the wound site is continuously under the prescribed pressure to facilitate healing.

From an examination of the skin surface at the ankle level, it is very easy to realize that the most prominent area at the ankle is the bony prominence, the medial malleolus. There is a similar bony prominence, the lateral malleolus, on the outer aspect of the ankle, but perhaps not so marked as the medial aspect. The heel and Achilles tendon also are prominent areas, and between the medial malleolus and the heel and the Achilles tendon, is a depression in the skin. A similar depression, or concavity, exists between the lateral malleolus and the heel and the Achilles tendon. When a support stocking is placed on the ankle, it places a great deal of pressure over the prominent areas, but there is a decreased pressure in the depressed areas, or the concavities, adjacent the medial malleolus and the lateral malleolus. Many of the chronic ulcers develop in the concavity adjacent the medial malleolus. The concavities are not compressed as well as the other areas because of the bony prominences.

Preferred embodiments of the present invention recognize the lack of adequate compression applied to these areas of concavity where ulcers develop and thus are directed to providing appropriate pressure to these specific wound sites. Further, these ulcers can include open sores present in the distal leg and foot that may have been caused by varicose vein disease, deep venous insufficiency, or a combination of both as described herein before. The open sores require appropriate wound care. Open sores can be caused by other problems including peripheral arterial disease or diabetes.

Figure 1:
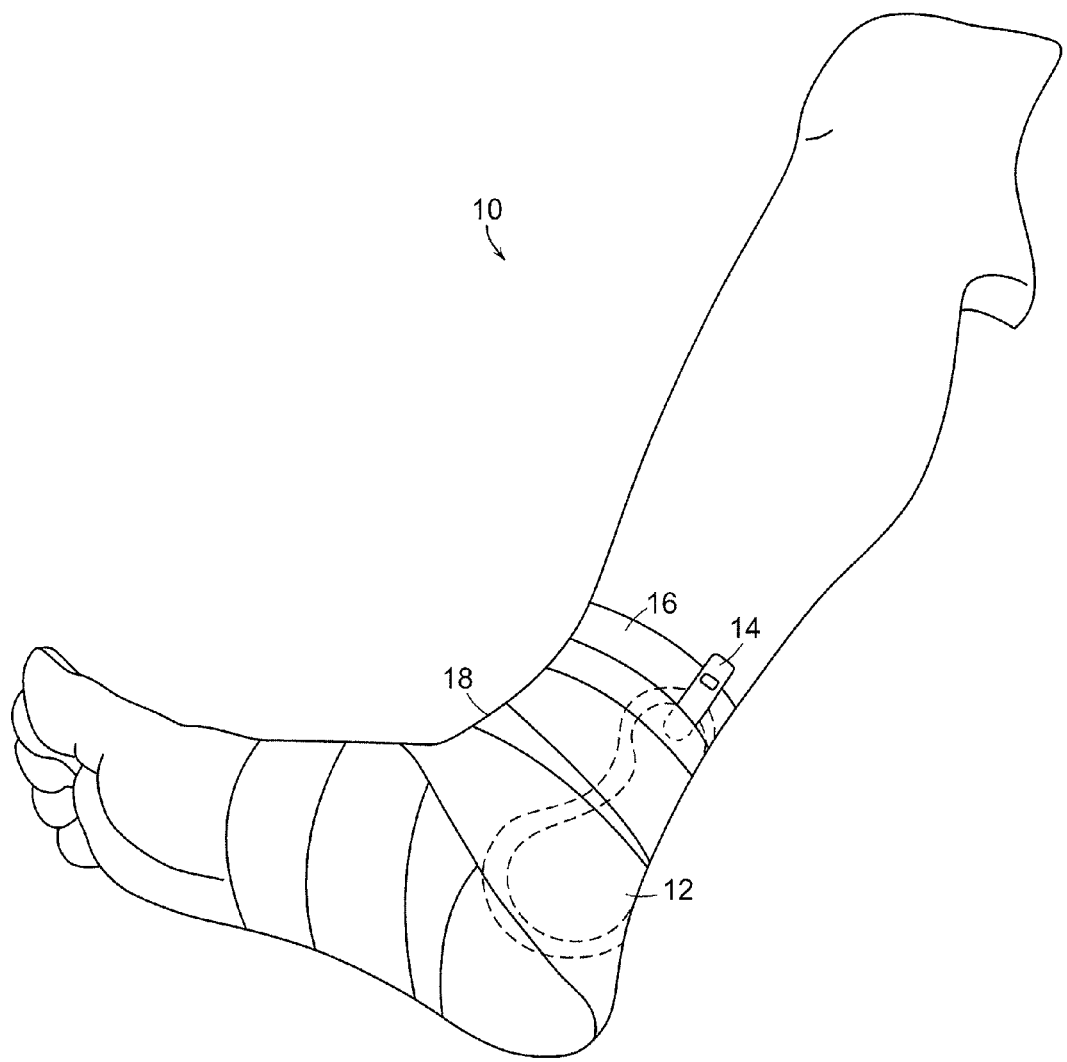
FIG. 1 is a side view of a right foot, ankle, and part of a leg of a human with a malleolar pad is in accordance with a preferred embodiment of the present invention.

FIG. 1 is a side view 10 of a right foot, ankle, and part of a leg of a human with a malleolar pad is in accordance with a preferred embodiment of the present invention. The malleolar pad 12 is applied on the medial (inner aspect) of the leg or ankle area 18. The malleolar pad has at least one pressure measurement device 14 to provide a measure of the pressure being applied by the malleolar pad, in particular to the wound site or ulcer. The malleolar pad 12 is secured using an elastic bandage 16 which in preferred embodiment may be integral with the pad or in alternate embodiments may be provided separately. The malleolar pad can also be provided in a stocking.

Figure 2:
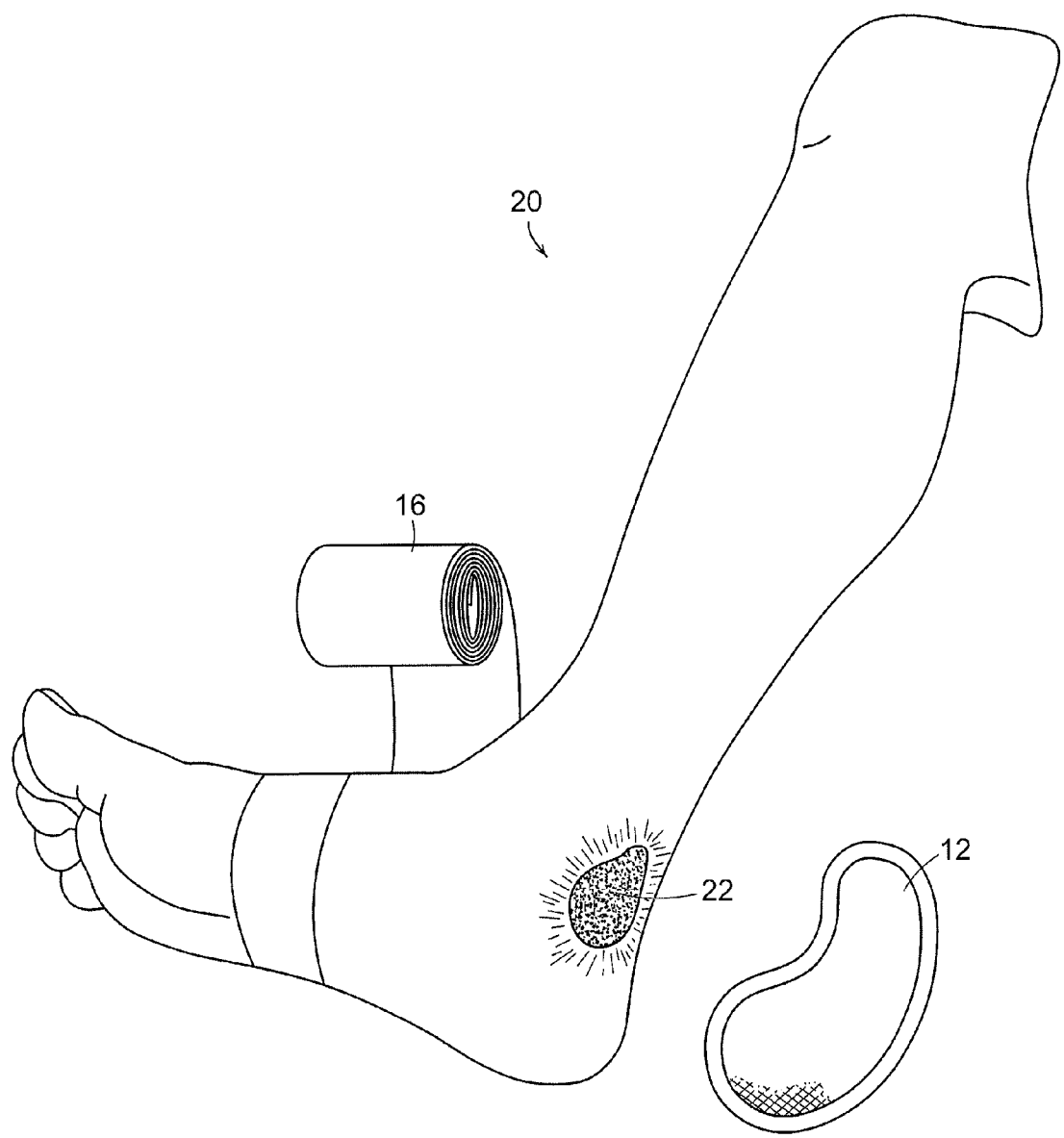
FIG. 2 is a view similar to FIG. 1 showing a venous ulcer and a malleolar pad in accordance with a preferred embodiment of the present invention that is applied onto the ulcerated region.

FIG. 2 is a view 20 similar to FIG. 1 showing a venous ulcer and a malleolar pad in accordance with a preferred embodiment of the present invention that is applied onto the ulcerated region. The wound site 22 may be an open sore. There is frequently brown discoloration of the skin as well as swelling, pain, and sometimes redness and dry, itchy skin at the wound site requiring appropriate wound care.

Figure 3:
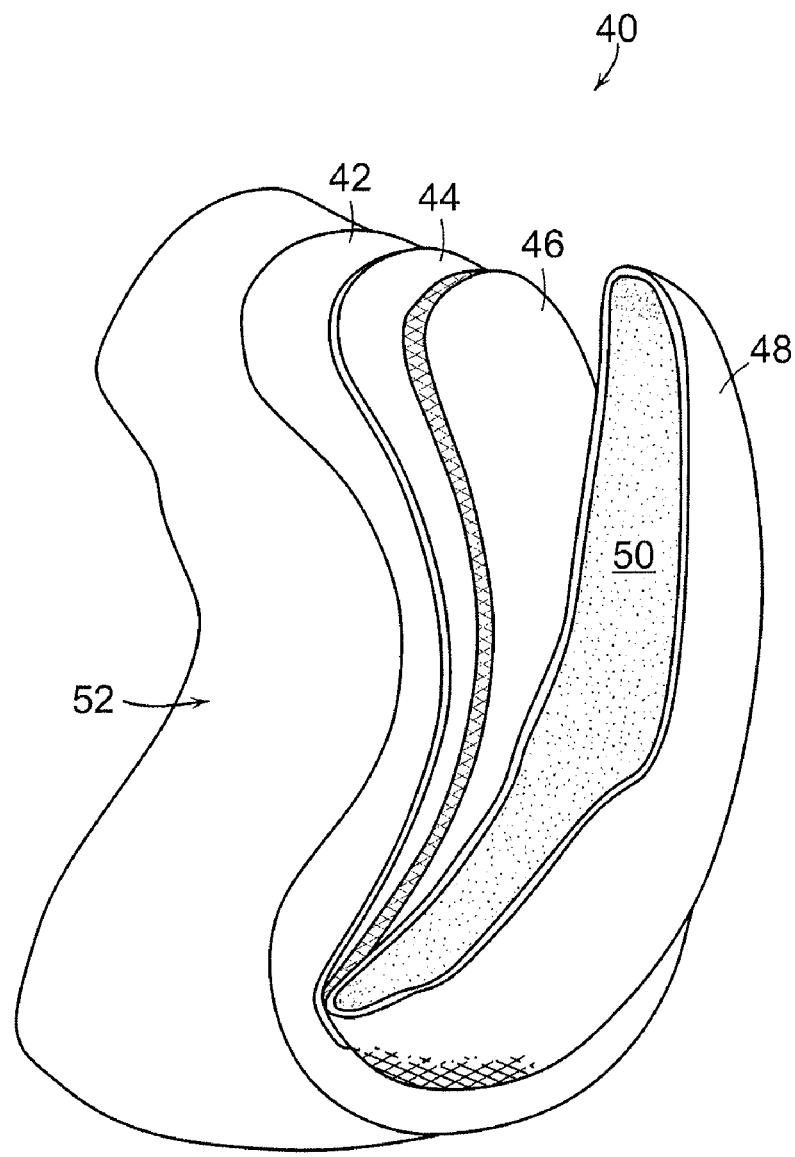
FIG. 3 is a cross-sectional view of a malleolar pad in accordance with a preferred embodiment of the present invention, illustrating the plurality of layers of the pad.

FIG. 3 is a cross-sectional view of a malleolar pad 40 in accordance with a preferred embodiment of the present invention, illustrating the plurality of layers of the pad. The malleolar pad 40 includes an adherent layer 42 to help in the application of the pad. It includes a non-adherent, absorbing layer 44 that is adjacent to a wicking layer 46. In a preferred embodiment, the absorbing layer 44 can be integral with the wicking layer 46. Preferred embodiments also include a drain port in fluid communication with the wicking layer to drain excessive serum or blood from the wound site. The wicking layer is made from bio-compatible materials. The pad 40 further includes a bladder or shell layer 48 that is filled with a tiller material 50 such as, for example, a gel that can be, for example, a silicon gel or polytetrafluoroethylene (PTFE). The gel-like substance has a flow characteristic that allows the pad to conform to the contour of the wound site. The pad 40 can be used on the elbow, head or upper or lower back 52.

Figure 4:
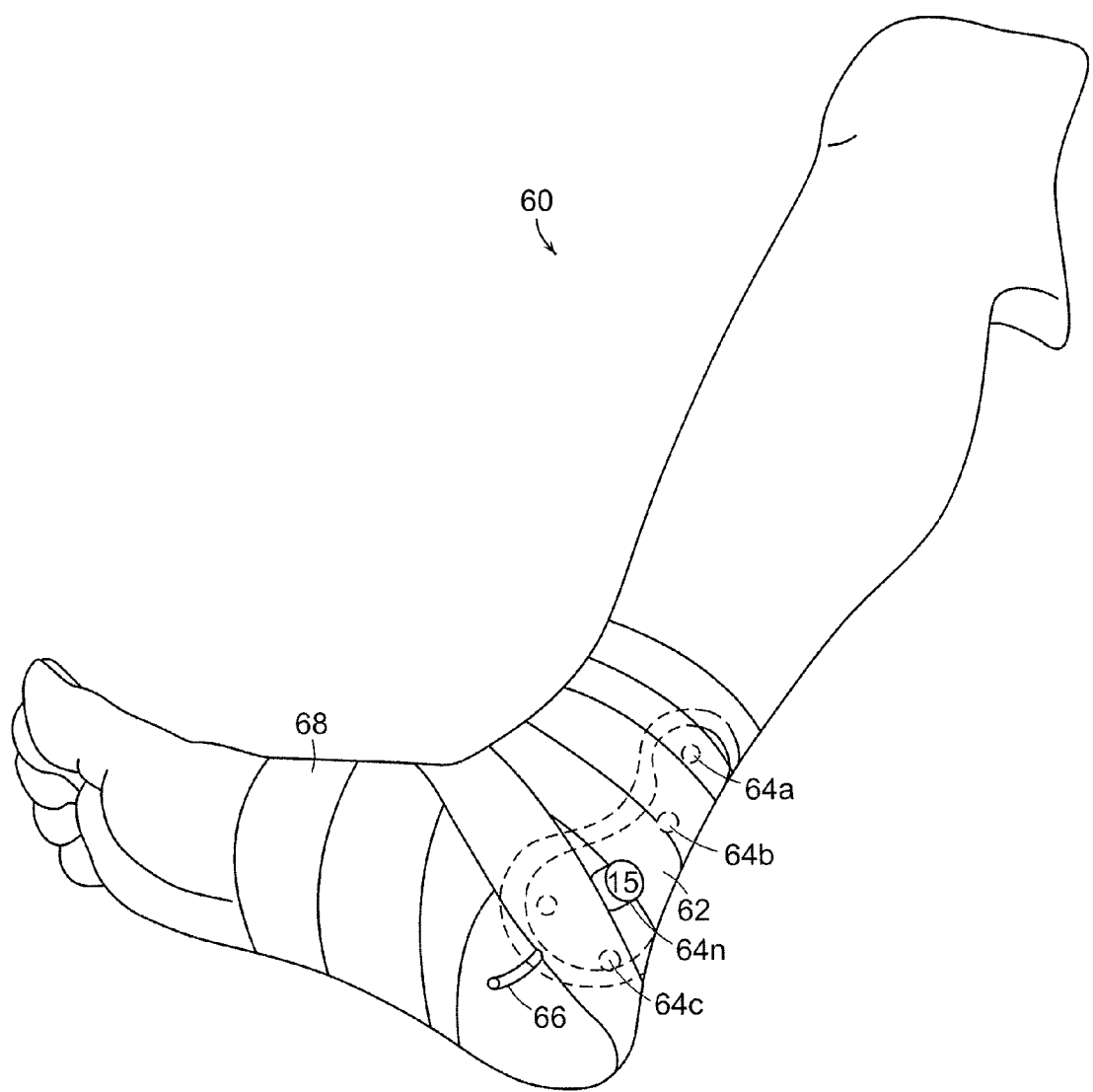
FIG. 4 illustrates the application of the malleolar pad having a digital pressure measurement device in accordance with a preferred embodiment of the present invention to the left leg, ankle and foot of a human.

FIG. 4 illustrates a sideview 60 of the application of the malleolar pad 62 and wrap 68 having a pressure measurement device having a digital readout in accordance with a preferred embodiment of the present invention to the left leg, ankle and foot of a human. Preferred embodiments include a plurality of pressure sensors or measurements devices such as, for example, a micro-array of pressure sensors 64a-n being positioned in the malleolar pad. Pressure measurement is thus provided for different sites including the open sore and sites around the sore. A conduit or drain port 66 can be provided in fluid communication with the wicking layer of the malleolar pad to remove excessive fluid. The pad 62 can be used on the elbow, head or upper or lower back 52.

Figure 5:
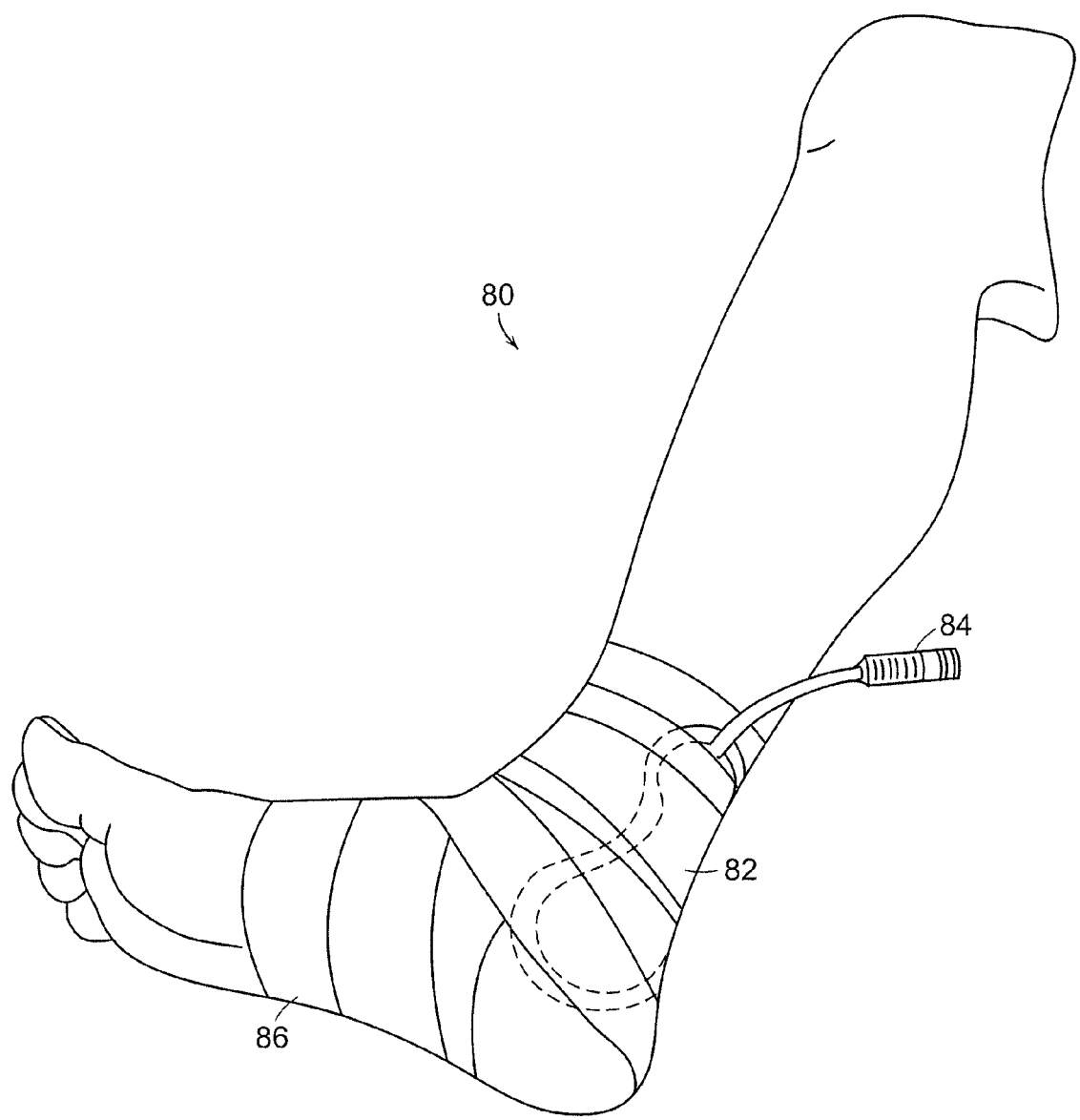
FIG. 5 illustrates the application of the malleolar pad having an analog pressure measurement device in accordance with a preferred embodiment of the present invention to the left leg, ankle and foot of a human.

FIG. 5 illustrates a side view 80 of the application of the malleolar pad 82 and wrap 86 having a pressure measurement device with an analog readout 84 in accordance with a preferred embodiment of the present invention to the left leg, ankle and foot of a human. The pressure measurement device is integral with the malleolar pad 82.

Figures 6A, 6B:
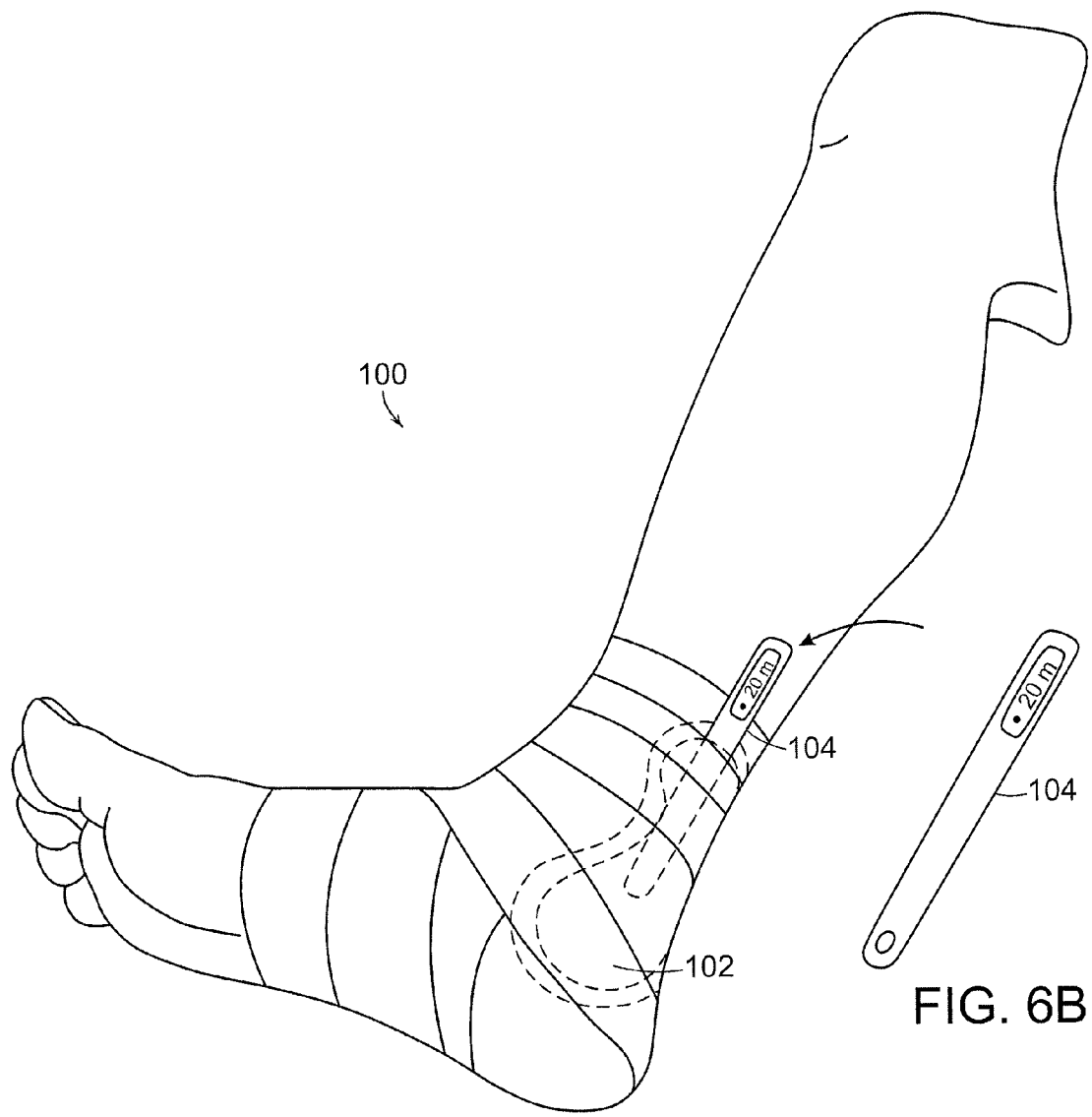
FIG. 6A illustrates the application of the malleolar pad having an alternative pressure measurement device in accordance with a preferred embodiment of the present invention to the left leg, ankle and foot of a human.
FIG. 6B illustrates the pressure measurement device shown in FIG. 6A in accordance with a preferred embodiment of the present invention.

FIG. 6A illustrates the application of the malleolar pad 102 having an alternative pressure measurement device 104 in accordance with a preferred embodiment of the present invention to the left leg, ankle and foot of a human. The pressure measurement device 104 is disposable and has a stick configuration that is easily removable. A replacement disposable pressure measurement device can be easily insertable in the pad of a preferred embodiment.

FIG. 6B illustrates the pressure measurement device shown in FIG. 6A in accordance with a preferred embodiment of the present invention.

Risk factors for developing venous insufficiency (inadequate venous function) and ultimately a venous ulcer include varicose veins, deep venous disease, incompetent perforating veins and post-thrombotic syndrome. While a non-healing ulcer of the medial (inner aspect) of the ankle area is discussed with respect to the figures, non-healing ulcers can be present in other areas as well. It is recognized that the invention described below can be used in other areas such as, for example, in the occipital region, in the sacrum, trochanter and isches donut or wherever a pressure ulcer can occur. Further, the pad in accordance with preferred embodiments can also be used to treat skin graft sites.

It is recognized that placing a controlled pressure on the skin counteracts the pressure in the veins. In addition, the pressure results in the superficial venous system being closer to the skin, therein allowing the absorption of oxygen through the skin. Wound healing is facilitated by and to a degree proportional to the amount of oxygen present in the proximate blood supply to the site. It is further recognized that the projection of the medial malleolus does not allow for pressure to be applied to the veins by a simple compression bandage.

The malleolar pad in accordance with the present invention provides the compressive force to the wound site and topographically distributes load in and around the wound site. The malleolar pad has a shape that conforms to the normal shape of the body region to which the pad is positioned. The malleolar pad includes mechanisms or features and material properties to facilitate the fitting of the pad to the body region.

The pad can have a taper near the ankle bone, such that the pad does not engage the body at the bone or the immediate adjacent area. This allows the pad to apply a pressure gradient in the depressed areas, or the concavities, adjacent the medial malleolus and the lateral malleolus. As described herein before, many of the chronic ulcers develop in the concavity adjacent the medial malleolus. The concavities are not compressed as well as the other areas because of the bony prominences.

The malleolar pad fills the depression and provides additional pressure to the medial and/or lateral sides of the leg, ankle and foot of a human being, in particular to the wound site. The pressure measurement device monitors the pressure which can be augmented at the wound site as necessary by further adjusting or tightening the bandaid or stocking used to secure and position the pad to the wound site. This allows for the simple application of the proper continuous pressure gradient to the wound site in the foot, ankle and leg of a patient, especially in the concave areas around the ankle.

The malleolar pad of the present invention is contoured to fill the concavities around the different wound sites or pressure ulcers as described herebefore. The contoured shape of the lateral ankle malleolar pad and the medial ankle malleolar pad, for example, completely fills the concavities such that pressure from the compression stockings is uniformly transmitted to the concavity.

A plurality of compression garments, for example, stockings or bandaids can be used to apply the malleolar pad of the preferred embodiments to a wound site.

It is recognized that the malleolar pad can be integrated with a single compression garment material such as a closed foam, for example, a polyurethane foam. In the alternative, the device includes a malleolar pad of the preferred embodiment and a separate compression wrapping. The pad is formed of bio-compatible material such as a PTFE or thermoplastic urethane (TPU).

In a preferred embodiment, two malleolar pads can be molded into an elastic stocking. A patient can simply slide it onto their foot to decrease pressure ulcers. The gel pads can be strategically placed to protect two wound sites simultaneously. The thin elastic sleeve holds pads securely in place and fits easily inside a shoe, boot or skate. Pressure can be augmented to particular sites by applying further compression wrapping by monitoring the pressure by a plurality of pressure measurement devices located integrally with the malleolar pads.

The claims should not be read as limited to the described order or elements unless stated to that effect. Therefore, all embodiments that come within the scope and spirit of the following claims and equivalents thereto are claimed as the invention.

What is claimed is:

1. A malleolar pad for treating a wound site in a region of the body comprising: a malleolar pad having a plurality of layers adapted to extend over a wound to facilitate treatment of the wound site, the plurality of layers including an adherent layer, a non-adherent layer proximate the adherent layer, a wicking layer, a bladder, and a filler layer disposed between the bladder; at least one pressure measurement device positioned in the malleolar pad that measures pressure; and a display connected to the pressure measurement device that numerically indicates pressure.

2. The malleolar pad of claim 1 wherein the filler layer comprises a gel or bio-compatible materials.

3. The malleolar pad of claim 1 wherein the wicking layer is in fluid communication with a conduit to remove fluid from the wound site.

4. The malleolar pad of claim 1 wherein the pressure measurement device has an analog readout or a digital readout.

5. The pad of claim 1 wherein the region of the body is proximate to the malleolar.

6. The pad of claim 1 wherein the region of the body is proximate to the elbow (epicondylar).

7. The pad of claim 1 wherein the region of the body is proximate to the back of the head (occipital).

8. The pad of claim 1 wherein the region of the body is proximate to the upper back (scapular).

9. The pad of claim 1 wherein the region of the body is proximate to the lower back (sacrum).

10. The pad of claim 1 further comprising a compression device formed of bio-compatible material.

11. The pad of claim 1 further comprising:
a compression wrapping for securing the malleolar pad with the region of the body, the pad shaped to conform to the shape of the body region.

12. A malleolar pad for treating a wound site in a region of the body comprising: a malleolar pad having plurality of layers adapted to extend over a wound to facilitate treatment of the wound site, the plurality of layers including a conforming filler layer, an adherent layer, a non-adherent layer proximate the adherent layer, a wicking layer, and a bladder enclosing the filler layer;

a compression device that applies pressure to the wound site; at least one pressure measurement device positioned in the malleolar pad that measures pressure; and a display connected to the pressure measurement device that numerically indicates pressure.

13. The malleolar pad of claim 12 wherein the filler layer comprises a gel or bio-compatible materials.

14. The malleolar pad of claim 12 wherein the wicking layer is in fluid communication with a conduit to remove fluid from the wound site.

15. The malleolar pad of claim 12 wherein the pressure measurement device has an analog readout or a digital readout.

16. The pad of claim 12 wherein the region of the body is proximate to the malleolar.

17. The pad of claim 12 wherein the region of the body is proximate to the elbow (epicondylar).

18. The pad of claim 12 wherein the region of the body is proximate to the back of the head (occipital).

* * * * *